United States Patent [19]

Takayama et al.

[11] 4,151,290
[45] Apr. 24, 1979

[54] FUNGICIDAL 1-CYCLOALKYLCARBONYL-3-(3,5-DIHALO-PHENYL)IMIDAZOLIDINE-2,4-DIONES

[75] Inventors: Chiyozo Takayama, Toyonaka; Toshiro Kato, Ibaraki; Shigeo Yamamoto, Ikeda; Yoshio Hisada, Kawanishi; Nobuyuki Kameda; Akira Fujinami, both of Takarazuka, all of Japan

[73] Assignee: Sumitomo Chemical Company, Limited, Osaka, Japan

[21] Appl. No.: 851,899

[22] Filed: Nov. 16, 1977

[30] Foreign Application Priority Data

Dec. 3, 1976 [JP] Japan .................. 51-145915

[51] Int. Cl.² ................... A61K 31/415; C07D 233/80
[52] U.S. Cl. .............................. 424/273 R; 548/312; 548/314
[58] Field of Search ...................... 548/312; 424/273 R

[56] References Cited

U.S. PATENT DOCUMENTS

| | | | |
|---|---|---|---|
| 3,161,652 | 12/1964 | Takamatsu et al. | 548/312 |
| 3,716,552 | 2/1973 | Fujinami et al. | 548/312 |
| 3,780,056 | 12/1973 | Singhal et al. | 548/312 |

Primary Examiner—Natalie Trousof
Assistant Examiner—Richard A. Schwartz
Attorney, Agent, or Firm—Birch, Stewart, Kolasch and Birch

[57] ABSTRACT

1-Cycloalkylcarbonyl-3-(3,5-dihalophenyl)imidazolidine-2,4-diones of the formula:

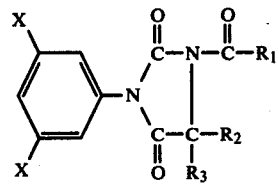

wherein X is a chlorine or bromine atom, $R_1$ is a $C_3$–$C_6$ cycloalkyl, tetramethylcyclopropyl, 2,2-dimethyl-3-isobutenylcyclopropyl or 2,2-dimethyl-3-dichlorovinylcyclopropyl group and $R_2$ and $R_3$ are individually a hydrogen atom or a methyl group, which show high fungicidal activities without any material toxicity to mammals and plants and which can be produced by reacting the corresponding 1-unsubstituted compound with a cycloalkanecarboxylic acid or a reactive derivative thereof.

8 Claims, No Drawings

FUNGICIDAL 1-CYCLOALKYLCARBONYL-3-(3,5-DIHALO-PHENYL)IMIDAZOLIDINE-2,4-DIONES

The present invention relates to 1-cycloalkylcarbonyl-3-(3,5-dihalophenyl)imidazolidine-2,4-diones (hereinafter referred to as "1-cycloalkylcarbonylimidazolidinedione(s)") of the formula:

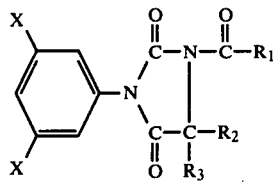

wherein X is a chlorine or bromine atom, $R_1$ is a $C_3$–$C_6$ cycloalkyl, tetramethylcyclopropyl, 2,2-dimethyl-3-isobutenylcyclopropyl or 2,2-dimethyl-3-dichlorovinylcyclopropyl group and $R_2$ and $R_3$ are individually a hydrogen atom or a methyl group, and their preparation and use.

It is already well known that some of the 3-(3,5-dihalophenyl)imidazolidine-2,4-dione derivatives, of which the 1- and 5-positions may be optionally substituted with various substituents, have a fungicidal activity on certain microoorganisms (U.S. Pat. Nos. 3,668,217 and 3,716,552). As the results of an extensive study, it has now been found that the said compounds [I] having a cycloalkylcarbonyl group at the 1-position exhibit a fungicidal activity which is widely applicable and markedly superior as compared with their homologues, and in addition show no material phytotoxicity to plants and a low mammalian toxicity.

The foregoing compounds, 1-cycloalkylcarbonylimidazolidinediones [I], are especially effective in controlling the diseases of agricultural and horticultural crops caused by the phytopathogenic fungi belonging to the Alternaria genus, such as black spot of pear (*Alternaria kikuchiana*), Alternaria leaf spot of apple (*Alternaria mali*), and early blight of tomato (*Alternaria solani*). In addition to the said diseases, several plant diseases which cause serious damages in agriculture and horticulture can be effectively controlled by the application of 1-cycloalkylcarbonylimidazolidinediones [I]. Those diseases include brown rot of peach (*Sclerotinia cinerea*), melanose of citrus (*Diaporthe citri*), common green mold of citrus fruits (*Penicillium digitatum*), blue mold of citrus fruits (*Penicillium italicum*), gray mold of grape (*Botrytis cinerea*), gray mold and Sclerotinia rot of beans and vegetables (*Botrytis cinerea* and *Sclerotinia sclerotiorum*) and the like.

Recently, the emergence of plant pathogens resistant to fungicides has been often noticed in fields, becoming a serious practical problem in crop protection with fungicide application. Then, 1-cycloalkylcarbonylimidazolidinediones [I] were found to exhibit a strong fungitoxicity towards those fungicide-resistant pathogens. For example, they have the same fungitoxic activity on the Polyoxin-resistant strain of *Alternaria kikuchiana* and the thiophanate-methyl[1,2-bis(3-methoxycarbonyl-2-thioureido)benzene]-resistant strain of *Botrytis cinerea* as on the respective wild strains (susceptible strains). It can be therefore expected that 1-cycloalkylcarbonylimidazolidinediones [I] exert prominent controlling effectiveness on plant diseases in the fields where fungicide-resistant pathogens have already emerged.

Furthermore, 1-cycloalkylcarbonylimidazolidinediones [I] possess a systemic property in plants. The compounds can penetrate from leaf surfaces into leaf tissues, and can be absorbed by roots and translocated to leaves. Due to this property, the compounds can effectively suppress propagation of the pathogens invading leaf tissues, in addition to protecting plants from infection.

The 1-cycloalkylcarbonylimidazolidinediones [I] of the present invention structurally relate to some of the compounds disclosed in U.S. Pat. No. 3,716,552, but their effectiveness in controlling the said diseases are superior to those of the latter compounds, and the 1-cycloalkylcarbonylimidazolidinediones [I] are still effective with the application at lower dosages. This indicates that substitution with a cycloalkylcarbonyl group at the 1-position of 3-(3,5-dihalophenyl)imidazolidine-2,4-dione derivatives resulted in marked increase in their fungitoxic activities. The present inventors are the first to point out this unexpected increase of activity.

A main object of the present invention is to provide novel 1-cycloalkylcarbonylimidazolidinediones [I], which are useful as fungicides. Another object of this invention is to provide a process for producing such 1-cycloalkylcarbonylimidazolidinediones [I]. A further object of the invention is to provide fungicidal compositions containing such 1-cycloalkylcarbonylimidazolidinediones [I]. These and other objects and advantages of the invention will become apparent from the foregoing and subsequent descriptions.

The 1-cycloalkylcarbonylimidazolidinediones [I] can be prepared by reacting the corresponding 1-unsubstituted compound of the formula:

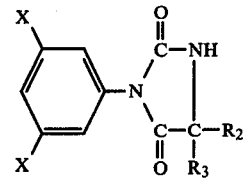

wherein X, $R_2$ and $R_3$ are each as defined above, with a cycloalkanecarboxylic acid of the formula:

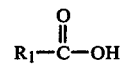

wherein $R_1$ is as defined above or a reactive derivative thereof. Usually, the reaction is effected between the said 1-unsubstituted compound [II] and a cycloalkanecarbonyl halide of the formula:

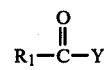

wherein $R_1$ is as defined above and Y is a halogen atom or a cycloalkylcarboxylic anhydride of the formula:

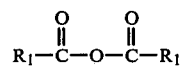

wherein $R_1$ is as defined above.

Examples of typical procedures for carrying out the said preparation so as to obtain the objective 1-cycloalkylcarbonylimidazolidinediones [I] in a good yield are as follows.

Procedure A

The starting 1-unsubstituted compound [II] is reacted with an equivalent or excessive molar amount of the cycloalkylcarbonyl halide [IV] at room temperature (0°–35° C.) in the presence or absence of a suitable solvent (e.g. tetrahydrofuran, methyl isobutyl ketone, benzene, toluene, xylene, chlorobenzene, chloroform, carbon tetrachloride, nitrobenzene) and, if necessary, in the presence of a dehydrohalogenating agent (e.g. triethylamine, N-methylmorpholine, pyridine, dimethylaniline, diethylaniline) and/or with heating (up to reflux) to give the 1-cycloalkylcarbonylimidazolidinedione [I].

Procedure B

The starting 1-unsubstituted compound [II] is reacted with an equivalent or excessive molar amount of the cycloalkylcarboxylic anhydride [V] at room temperature (0°–35° C.) in the presence or absence of a suitable solvent (e.g. chloroform, carbon tetrachloride, benzene, toluene, xylene, ligroin) and, if necessary, with heating to give the 1-cycloalkylcarbonylimidazolidinedione [I].

The 1-cycloalkylcarbonylimidazolidinedione [I] thus produced may be purified, if necessary, by a per se conventional procedure such as recrystallization from a proper solvent.

The starting 1-unsubstituted compound [II] is obtainable, for instance, by the process as described in U.S. Pat. No. 3,668,217.

In actual application as fungicides, the 1-cycloalkylcarbonylimidazolidinediones [I] may be used alone without incorporation of any other ingredients such as carriers and diluents or, for easier application, in admixture with such solid carriers or diluents as talc, clay and the like or with such liquid carriers or diluents as organic solvents and the like. The fungicidal compositions can be formulated into any of the ordinarily adopted forms such as, for example, dusts, wettable powders, oil sprays, aerosols, tablets, emulsifiable concentrates and granules.

The foregoing preparations generally contain 0.1 to 95.0% by weight, preferably 0.2 to 90.0% by weight, of the active ingredient (including other ingredients mixed therewith). A suitable amount of the preparations applied is generally 10 g to 1000 g/10 are, and the concentration of the preparations applied is preferably within the range of 0.001 to 0.1% by weight. Since, however, the amount and concentration depend upon the preparation forms, application times, application methods, application sites, diseases and crops, they may be properly increased or decreased irrespective of the aforesaid ranges.

Further, the 1-cycloalkylcarbonylimidazolidinediones [I] may be used in admixture with other fungicides such as, for example, N-(3,5-dichlorophenyl)-1,2-dimethylcyclopropane-1,2-dicarboximide, S-n-butyl-S'-p-tert-butylbenzyl-N-3-pyridyldithiocarbonimidate, O,O-dimethyl-O-2,6-dichloro-4-methylphenylphosphorothioate, methyl N-benzimidazol-2-yl-N-(butylcarbamoyl)-carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene and the like; and the 1-cycloalkylcarbonylimidazolidinediones [I] may be used in admixture with insecticides such as, for example, O,O-dimethyl-O-(4-nitro-m-tolyl)phosphorothioate, O-p-cyanophenyl-O,O-dimethylphosphorothioate, O-p-cyanophenyl-O-ethylphenylphosphonothioate, O,O-dimethyl-S-(N-methylcarbamoylmethyl)phosphorodithioate, 2-methoxy-4H-1,3,2-benzodioxaphosphorine-2-sulfide, O,O-dimethyl-S'-(1-ethoxycarbonyl-1-phenylmethyl)phosphorodithioate, α-cyano-3-phenoxybenzyl-2-(4-chlorophenyl) isovalerate, 3-phenoxybenzyl-2,2-dimethyl-3-(2,2-dichlorovinyl)cyclopropanecarboxylate, 3-phenoxybenzyl chrysanthemate and the like; and, in every case, no controlling effects of individual chemicals are decreased. Accordingly, simultaneous control of two or more pests and injurious insects is possible. In addition thereto, they may be used in admixture with such agricultural chemicals as nematocides and acaricides and with fertilizers.

Practical and presently preferred embodiments of the present invention are illustratively shown in the following examples, wherein parts and % are by weight.

EXAMPLE 1

Preparation of the 1-cycloalkylcarbonylimidazolidinediones [I]:

Procedure A 0.05 mole of a 3-(3,5-dihalophenyl)imidazolidine-2,4-dione derivative of the formula [II] and 0.06 mole of triethylamine are dissolved in 150 ml of toluene, and 0.06 mole of an acid chloride of the formula [IV] is added thereto dropwise slowly at room temperature with stirring. After the addition is finished, the mixture is heated under reflux for 7 hours. The reaction mixture is filtered, and the filtrate is concentrated under reduced pressure. The residue obtained is well washed with water, and the water-insoluble portion is collected by filtration and dried to obtain the objective 1-cycloalkylcarbonyl-3-(3,5-dihalophenyl)imidazolidine-2,4-dione derivative of the formula [I] in a high yield. The crude product is recrystallized from ethanol to obtain a pure product.

Procedure B 0.05 mole of a 3-(3,5-dihalophenyl)imidazolidine-2,4-dione derivative of the formula [II] and 0.15 mole of an acid anhydride of the formula [V] are dissolved in 50 ml of toluene. The mixture is heated under reflux for 15 hours. After the reaction is finished, the reaction solution is cooled to room temperature and poured into water saturated with sodium hydrogen carbonate, followed by stirring for some time. The solid material obtained is collected by filtration, washed with water several times and dried to obtain the objective 1-cycloalkylcarbonyl-3-(3,5-dihalophenyl)imidazolidine-2,4-dione derivative of the formula [I] in a high yield. The crude product is recrystallized from ethanol to obtain a pure product.

According to either one of the above procedures, the 1-cycloalkylcarbonylimidazolidinediones [I] as shown in Table 1 are prepared.

Table 1

| | Starting materials | | 1-Cycloalkylcarbonyl-3-(3,5-dihalophenyl)imidazolidine-2,4-dione compound [I] | | | | | | |
|---|---|---|---|---|---|---|---|---|---|
| Procedure | 3-(3,5-Dihalophenyl)imidazolidiene-2,4-dione compound [III] | Acid chloride [IV] or acid anhydride [V] | Compound No. | Chemical structure | Melting point (°C.) | Yield (%) | \multicolumn{3}{c|}{Elementary analysis (%)} | |
| | | | | | | | C | H | N | Halogen |
| A | [3,5-dichlorophenyl hydantoin] | cyclopropanecarbonyl chloride | 1 | [1-cyclopropylcarbonyl-3-(3,5-dichlorophenyl)hydantoin] | 154.5–156.0 | 90 | 49.86 (49.68) | 3.22 (3.13) | 8.95 (8.82) | (Cl) 22.64 (22.61) |
| A | [3,5-dichlorophenyl hydantoin] | cyclobutanecarbonyl chloride | 2 | [1-cyclobutylcarbonyl-3-(3,5-dichlorophenyl)hydantoin] | 101.5–104.5 | 72 | 51.40 (51.23) | 3.70 (3.52) | 8.56 (8.39) | (Cl) 21.67 (21.86) |
| A | [3,5-dichlorophenyl hydantoin] | cyclopentanecarbonyl chloride | 3 | [1-cyclopentylcarbonyl-3-(3,5-dichlorophenyl)hydantoin] | 102.0–103.0 | 83 | 52.80 (52.65) | 4.14 (4.11) | 8.21 (8.38) | (Cl) 20.78 (20.91) |
| A | [3,5-dichlorophenyl hydantoin] | cyclohexanecarbonyl chloride | 4 | [1-cyclohexylcarbonyl-3-(3,5-dichlorophenyl)hydantoin] | 159.5–161.0 | 87 | 54.10 (53.97) | 4.54 (4.34) | 7.89 (7.80) | (Cl) 19.96 (19.90) |
| A | [3,5-dichlorophenyl hydantoin] | 2,2,3,3-tetramethylcyclopropanecarbonyl chloride | 5 | [1-(2,2,3,3-tetramethylcyclopropylcarbonyl)-3-(3,5-dichlorophenyl)hydantoin] | 128.5–131.0 | 89 | 55.30 (55.51) | 4.91 (5.00) | 7.59 (7.43) | (Cl) 19.20 (18.86) |

Table 1-continued

| Procedure | Starting materials | | Compound No. | 1-Cycloalkylcarbonyl-3-(3,5-dihalophenyl)imidazolidine-2,4-dione compound [II] | | | Elementary analysis (%) | | | |
| --- | --- | --- | --- | --- | --- | --- | --- | --- | --- | --- |
| | 3-(3,5-Dihalophenyl)imidazolidiene-2,4-dione compound [II] | Acid chloride [IV] or acid anhydride [V] | | Chemical structure | Melting point (°C.) | Yield (%) | C | H | N | Halogen |
| A | [structure] | [structure] | 6 | [structure] | 122.0–125.0 | 78 | 57.73 (57.96) | 5.10 (4.98) | 7.09 (7.21) | (Cl) 17.94 (18.00) |
| A | [structure] | [structure] | 7 | [structure] | 119.0–144.5 | 81 | 46.82 (46.70) | 3.24 (3.20) | 6.42 (6.33) | (Cl) 32.52 (32.31) |
| A | [structure] | [structure] | 8 | [structure] | 121–122 | 85 | 51.40 (51.29) | 3.70 (3.71) | 8.56 (8.42) | (Cl) 21.67 (21.62) |
| B | [structure] | [structure] | 9 | [structure] | 110.5–113.5 | 83 | 55.30 (55.49) | 4.91 (5.08) | 7.59 (7.36) | (Cl) 19.20 (19.31) |

Table 1-continued

1-Cycloalkylcarbonyl-3-(3,5-dihalophenyl)imidazolidine-2,4-dione compound [I]

| Procedure | Starting materials 3-(3,5-Dihalophenyl)imidazolidiene-2,4-dione compound [II] | Acid chloride [IV] or acid anhydride [V] | Compound No. | Chemical structure | Melting point (°C.) | Yield (%) | Elementary analysis (%) C | H | N | Halogen |
|---|---|---|---|---|---|---|---|---|---|---|
| A | (3,5-dichlorophenyl imidazolidinedione with CH₃/CH₃) | cyclopropyl-C(=O)-Cl | 10 | (1-cyclopropylcarbonyl-3-(3,5-dichlorophenyl)-5,5-dimethylimidazolidine-2,4-dione) | 96.5–97.5 | 92 | 52.80 (52.64) | 4.14 (4.08) | 8.21 (8.10) | (Cl) 20.78 (20.72) |
| A | (3,5-dibromophenyl imidazolidinedione with H/H) | cyclopropyl-C(=O)-Cl | 11 | (1-cyclopropylcarbonyl-3-(3,5-dibromophenyl)imidazolidine-2,4-dione) | 140.5–143.5 | 77 | 38.84 (38.61) | 2.51 (2.35) | 6.97 (7.11) | (Cl) 39.75 (39.88) |

In the elemental analysis, the values as calculated are unparenthesized, and the values as found are parenthesized.

EXAMPLE 2

Formulation of compositions:

(a) Dust

2 Parts of the compound (8) and 98 parts of clay were thoroughly pulverized and mixed together to obtain a dust containing 2% of the active ingredient. In application, the dust was dusted as such.

(b) Dust

3 Parts of the compound (4) and 97 parts of talc were thoroughly pulverized and mixed together to obtain a dust containing 3% of the active ingredient. In application, the dust was dusted as such.

(c) Wettable powder

50 Parts of the compound (1), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

(d) Emulsifiable concentrate

10 Parts of the compound (2), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

(e) Granule

5 Parts of the compound (10), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the 1-cycloalkylcarbonylimidazolidinediones [I]. In these examples, the compound numbers correspond to those in Table 1.

EXAMPLE 3

Fungicidal activity test on fungicide-resistant pathogens:

Ten milliliters of a potato sucrose agar medium was turned into a solution by heating, and each of the emulsifiable concentrates containing the test compounds was added to the solution and well mixed. The mixture was flowed into a glass Petri dish of 9 cm in diameter to make an agar plate. After the agar was hardened, mycelial discs (5 mm in diameter) of a fungicide-resistant strain of gray mold fungus (*Botrytis cinerea*) resistant to 1,2-bis(3-methoxycarbonyl-2-thioureido)benzene which was isolated from grapes and a wild (susceptible) strain of *Botrytis cinerea* were each placed at the center of the agar plate and incubated at 20° C. for 3 days. After the incubation, the diameter of the grown colony was measured, and the percentage of growth inhibition was calculated from the following equation in comparison with an untreated plot:

$$\text{Percentage of growth inhibition (\%)} = 100 - \frac{\text{Diameter of colony in treated}}{\text{Diameter of colony in untreated plot}} \times 100$$

As the result, the compounds of the present invention showed a strong antimicrobial activity on a fungicide-resistant strain of *Botrytis cinerea* as well as on a susceptible wild strain of *Botrytis cinerea*, as shown in Table 2.

Table 2

| Compound No. | Fungicidal effect on a wild (susceptible) strain of *Botrytis cinerea* | | Fungicidal effect on a fungicide-resistant strain of *Botrytis cinerea*[1] | |
|---|---|---|---|---|
| | Concentration of pesticide in medium (concentration of active ingredient) (ppm) | Percentage of growth inhibition (%) | Concentration of pesticide in medium (concentration of active ingredient) (ppm) | Percentage of growth inhibition (%) |
| 1 | 10 | 94 | 10 | 94 |
| | 1 | 94 | 1 | 94 |
| 2 | 10 | 94 | 10 | 94 |
| | 1 | 92 | 1 | 90 |
| 4 | 10 | 94 | 10 | 94 |
| | 1 | 90 | 1 | 92 |
| 5 | 10 | 94 | 10 | 94 |
| | 1 | 90 | 1 | 88 |
| 6 | 10 | 94 | 10 | 94 |
| | 1 | 85 | 1 | 83 |
| 7 | 10 | 94 | 10 | 94 |
| | 1 | 78 | 1 | 80 |
| 8 | 10 | 94 | 10 | 94 |
| | 1 | 92 | 1 | 90 |
| 9 | 10 | 94 | 10 | 94 |
| | 1 | 88 | 1 | 90 |
| 10 | 10 | 94 | 10 | 94 |
| | 1 | 89 | 1 | 85 |
| 11 | 10 | 94 | 10 | 94 |
| | 1 | 94 | 1 | 94 |
| Thio-[2] phanate-methyl | 10 | 94 | 100 | 32 |
| | 1 | 70 | 10 | 10 |
| | | | 1 | 0 |

Notes:
[1] Strain resistant to 1,2-bis(3-methoxycarbonyl-2-thioureido)benzene (isolated from grapes)
[2] Commercially available fungicide, 1,2-bis(3-methoxycarbonyl-2-thioureido)benzene.

EXAMPLE 4

Protective activity test on black spot of pear (*Alternaria kikuchiana*):

A 3-year old pear tree (var.: 20-Seiki) cultivated in a flower pot of 30 cm in diameter was used as a test plant.

Each of the emulsifiable concentrates containing the test compounds was diluted with water to a required concentration. When each plant shot out three to four young branches having 10 to 20 leaves thereon, the prepared aqueous solution was sprayed thereon in a rate of 30 ml/seedling. The plant was cultivated in a greenhouse for 7 days after spraying. The whole body of the plant was then inoculated by spraying the spore suspension of *Alternaria kikuchiana* cultured in a vegetable juice agar medium for 10 days. The plant was then placed in a humid chamber for 24 hours after inoculation and then in a green-house for 2 days. The disease severity was examined as follows using a disease index (0, 1, 2, 3, 4, 5):

| Disearse severity | Disease index |
|---|---|
| No infected area | 0 |
| Infected leaf area of less than 10% | 1 |
| Infected leaf area of 10 to less than 20% | 2 |
| Infected leaf area of 20 to less than 40% | 3 |
| Infected leaf area of 40 to less than 60% | 4 |
| Infected leaf area of 60% or more | 5 |

The disease severity was calculated according to the following equation:

$$\text{Disease severity (\%)} = \frac{\Sigma \text{(Disease index)} \times \text{(Number of leaves)}}{5 \times \text{(Total number of leaves examined)}} \times 100$$

As a result, the compounds of the present invention were much superior in the protective activity to the control compounds tested at the same time, as shown in Table 3.

Table 3

| Compound No. | Concentration of active ingredient (ppm) | Disease severity (%) |
|---|---|---|
| 1 | 1000 | 0.0 |
|   | 100 | 1.0 |
| 2 | 1000 | 0.5 |
|   | 100 | 3.2 |
| 3 | 1000 | 0.8 |
|   | 100 | 3.0 |
| 4 | 1000 | 1.0 |
|   | 100 | 2.8 |
| 5 | 1000 | 1.0 |
|   | 100 | 4.5 |
| 6 | 1000 | 1.6 |
|   | 100 | 5.0 |
| 7 | 1000 | 0.5 |
|   | 100 | 2.5 |
| 8 | 1000 | 0.8 |
|   | 100 | 4.0 |
| 9 | 1000 | 2.0 |
|   | 100 | 5.5 |
| 10 | 1000 | 2.5 |
|   | 100 | 6.8 |
| 11 | 1000 | 0.0 |
|   | 100 | 2.5 |
| 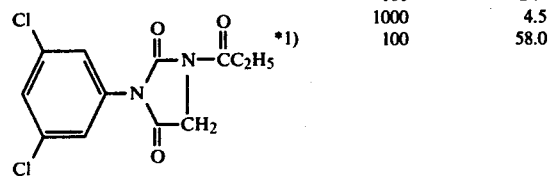 *1) | 1000 | 4.5 |
|   | 100 | 58.0 |

Table 3-continued

| Compound No. | Concentration of active ingredient (ppm) | Disease severity (%) |
|---|---|---|
| [structure] *2) | 1000 | 5.0 |
|   | 100 | 63.2 |
| No treatment | — | 72.5 |

Note:
*1) Compound disclosed in U.S. Pat. No. 3,716,552.
*2) Commercially available fungicide, generic name "Captafol".

EXAMPLE 4

Protective activity test on stem rot of kidney bean (*Sclerotinia sclerotiorum*):

Kidney beans (var.: Taishō-kintoki) were grown up to the two-leaf stage in a flower pot of 15 cm in diameter. Each of the emulsifiable concentrates containing the test compounds was diluted with water and sprayed on the kidney beans in a rate of 10 cm/pot. After the kidney beans were air-dried for 4 hours, they were inoculated with the mycelial disc (5 mm in diameter) of *Sclerotinia sclerotiorum*. After the inoculation, the test plants were infected by placing them under a highly humid, dark condition at 20° C. for 4 days. The disease severity was calculated on the basis of the following standard for evaluating infection:

| Disease index | Evaluation of infection |
|---|---|
| 0 | No infection |
| 1 | Slight infection around the inoculum |
| 2 | Infected area of about 1/6 of the inoculated leaf |
| 3 | Infected area of about 2/5 of the inoculated leaf |
| 4 | Infected area of about 3/5 of the inoculated leaf |
| 5 | Infected area of 3/5 or more of the inoculated leaf |

$$\text{Disease severity (\%)} = \frac{\Sigma \text{(Disease index)} \times \text{(Number of leaves)}}{5 \times \text{(Total number of leaves examined)}} \times 100$$

As the result, the compounds of the present invention were superior in the protective activity to the control compound tested at the same time, as shown in Table 4.

Table 4

| Compound No. | Concentration of active ingredient (ppm) | Disease severity (%) |
|---|---|---|
| 1 | 100 | 0.0 |
| 2 | 100 | 0.0 |
| 4 | 100 | 2.5 |
| 5 | 100 | 0.0 |
| 6 | 100 | 0.0 |
| 7 | 100 | 2.5 |
| 8 | 100 | 0.0 |
| 9 | 100 | 0.0 |
| 10 | 100 | 2.5 |
| 11 | 100 | 0.0 |

Table 4-continued

| Compound No. | Concentration of active ingredient (ppm) | Disease severity (%) |
| --- | --- | --- |
| Cl, O₂N, NH₂, Cl structure *1) | 100 | 47.5 |
| No treatment | — | 100.0 |

Note:
*1) Commercially available fungicide, generic name "Dcna".

EXAMPLE 5

Protective activity test on blue mold of orange (*Penicillium italicum*):

Orange fruits (var.: Unshū) were well washed with water and air-dried. Each of the emulsifiable concentrates containing the test compounds was diluted with water to a required concentration and the air-dried orange fruits were dipped in the aqueous solution for 1 minute. After air-drying, the surface of the fruit was inoculated by spraying a spore suspension of *Penicillium italicum* cultured in a potato agar medium for 5 days. After the fruits were placed in a humid chamber for 7 days after inoculation, the disease severity was examined using a disease index (0, 1, 2, 3, 4, 5). The results were shown in the mean value of disease index.

| Disease severity | Disease index |
| --- | --- |
| No infected area | 0 |
| Infected surface area of less than 20% | 1 |
| Infected surface area of 20 to less than 40% | 2 |
| Infected surface area of 40 to less than 60% | 3 |
| Infected surface area of 60 to less than 80% | 4 |
| Infected surface area of 80% or more | 5 |

As the result, the compounds of the present invention were superior in the protective activity to the control compounds tested at the same time, as shown in Table 5.

Table 5

| Compound No. | Concentration of active ingredient (ppm) | Mean value of disease index |
| --- | --- | --- |
| 1 | 100 | 0.0 |
| 2 | 100 | 0.0 |
| 4 | 100 | 0.0 |
| 5 | 100 | 0.8 |
| 6 | 100 | 0.5 |
| 7 | 100 | 1.3 |

Table 5-continued

| Compound No. | Concentration of active ingredient (ppm) | Mean value of disease index |
| --- | --- | --- |
| 8 | 100 | 0.0 |
| 9 | 100 | 0.0 |
| 10 | 100 | 0.2 |
| 11 | 100 | 0.0 |
| Cl, N-CCH₃ structure *1) | 200 | 2.6 |
| Cl, N-CC₂H₅ structure *2) | 200 | 3.1 |
| No treatment | — | 5.0 |

Note:
*1) & *2) Compounds disclosed in U.S. Pat. No. 3,716,552.

What is claimed is:

1. A compound of the formula:

$$X\text{-}\underset{X}{\underset{|}{\bigcirc}}\text{-}N\underset{\underset{O}{\parallel}}{\overset{\overset{O}{\parallel}}{\underset{C}{\overset{C}{-}}}}\underset{R_3}{\overset{}{\underset{|}{C}}}\text{-}\underset{}{\overset{O}{\parallel}}\overset{}{\underset{}{C}\text{-}R_1}\;\;\; \text{and}\;\; \text{-}C\text{-}R_2$$

wherein X is a chlorine or bromine atom, $R_1$ is a $C_3$–$C_6$ cycloalkyl, tetramethylcyclopropyl, 2,2-dimethyl-3-isobutenylcyclopropyl or 2,2-dimethyl-3-dichlorovinyl-cyclopropyl group and $R_2$ and $R_3$ are individually a hydrogen atom or a methyl group.

2. The compound according to claim 1, wherein X is a chlorine atom, $R_1$ is a $C_3$–$C_6$ cycloalkyl group and $R_2$ and $R_3$ are each a hydrogen atom.

3. The compound according to claim 1, wherein X is a chlorine atom, $R_1$ is a cyclopropyl group and $R_2$ and $R_3$ are each a hydrogen atom.

4. The compound according to claim 1, wherein X is a chlorine atom, $R_1$ is a cyclobutyl group and $R_2$ and $R_3$ are each a hydrogen atom.

5. The compound according to claim 1, wherein X is a chlorine atom, $R_1$ is a cyclopentyl group and $R_2$ and $R_3$ are each a hydrogen atom.

6. The compound according to claim 1, wherein X is a chlorine atom, $R_1$ is a cyclohexyl group and $R_2$ and $R_3$ are each a hydrogen atom.

7. A fungicidal composition which comprises as an active ingredient a fungicidally effective amount of the compound according to claim 1 and an inert carrier.

8. A method for controlling fungi which comprises applying a fungicidally effective amount of the compound according to claim 1 to the fungi.

* * * * *